United States Patent
Householder et al.

(10) Patent No.: US 11,160,538 B2
(45) Date of Patent: Nov. 2, 2021

(54) BIOPSY DEVICE WITH LINEAR ACTUATOR

(71) Applicant: Devicor Medical Products, Inc., Cincinnati, OH (US)

(72) Inventors: Robert M. Householder, Loveland, OH (US); John Kevin Bruce, Burlington, KY (US)

(73) Assignee: Devicor Medical Products, Inc., Cincinnati, OH (US)

( * ) Notice: Subject to any disclaimer, the term of this patent is extended or adjusted under 35 U.S.C. 154(b) by 570 days.

(21) Appl. No.: 15/796,970

(22) Filed: Oct. 30, 2017

(65) Prior Publication Data

US 2018/0116644 A1    May 3, 2018

Related U.S. Application Data

(60) Provisional application No. 62/414,986, filed on Oct. 31, 2016.

(51) Int. Cl.
*A61B 10/02* (2006.01)
*A61B 34/20* (2016.01)
*A61B 17/00* (2006.01)

(52) U.S. Cl.
CPC ...... *A61B 10/0266* (2013.01); *A61B 10/0275* (2013.01); *A61B 34/20* (2016.02); *A61B 2010/0208* (2013.01); *A61B 2017/00398* (2013.01); *A61B 2034/2051* (2016.02)

(58) Field of Classification Search
CPC ............ A61B 10/0266; A61B 10/0275; A61B 2017/00398; A61B 2010/0208
See application file for complete search history.

(56) References Cited

U.S. PATENT DOCUMENTS

| | | |
|---|---|---|
| 5,526,822 A | 6/1996 | Burbank et al. |
| 5,928,164 A | 7/1999 | Burbank et al. |
| 6,017,316 A | 1/2000 | Ritchart et al. |
| 6,086,544 A | 4/2000 | Hibner et al. |
| 6,162,187 A | 12/2000 | Buzzard et al. |
| 6,432,065 B1 | 8/2002 | Burdorff et al. |
| 6,551,255 B2 | 4/2003 | Van Bladel et al. |
| 6,626,849 B2 | 9/2003 | Huitema et al. |

(Continued)

FOREIGN PATENT DOCUMENTS

| | | | |
|---|---|---|---|
| EP | 2260767 | 12/2010 | |
| EP | 2260767 A1 * | 12/2010 | ......... A61B 10/0275 |

OTHER PUBLICATIONS

Hahn, M., et al., "Diagnostic Primer: Vacuum-Assisted Breast Biopsy with Mammotome®," Devicor Medical Germany GmBh, Nov. 11, 2012, Germany, Springer Medizin Verlag, copyright 2013, 130 pgs.

(Continued)

*Primary Examiner* — Sean P Dougherty
(74) *Attorney, Agent, or Firm* — Frost Brown Todd LLC

(57) ABSTRACT

A cutter actuation assembly for actuating a cutter of a biopsy device includes a cutter sleeve, a receiving member, and a linear actuator. The cutter sleeve is fixedly secured to the cutter of the biopsy device. The receiving member is configured to receive at least a portion of the cutter sleeve. The linear actuator is configured to translate the cutter sleeve. The receiving member is configured to rotate the cutter sleeve as the cutter sleeve is translated relative to the receiving member.

20 Claims, 9 Drawing Sheets

(56) References Cited

U.S. PATENT DOCUMENTS

| | | |
|---|---|---|
| 6,752,768 B2 | 6/2004 | Burdorff et al. |
| 7,252,264 B2 | 8/2007 | Thompson et al. |
| 7,442,171 B2 | 10/2008 | Stephens et al. |
| 7,507,210 B2 | 3/2009 | Hibner et al. |
| 7,648,466 B2 | 1/2010 | Stephens et al. |
| 7,708,751 B2 | 5/2010 | Hughes et al. |
| 7,831,290 B2 | 11/2010 | Hughes et al. |
| 7,837,632 B2 | 11/2010 | Stephens et al. |
| 7,854,706 B2 | 12/2010 | Hibner |
| 7,914,464 B2 | 3/2011 | Burdorff et al. |
| 7,918,804 B2 | 4/2011 | Monson et al. |
| 7,938,786 B2 | 5/2011 | Ritchie et al. |
| 8,083,687 B2 | 12/2011 | Parihar |
| 8,118,755 B2 | 2/2012 | Hibner et al. |
| 8,167,815 B2 | 5/2012 | Parihar |
| 8,177,728 B2 | 5/2012 | Hibner et al. |
| 8,206,316 B2 | 6/2012 | Hibner et al. |
| 8,241,226 B2 | 8/2012 | Hibner et al. |
| 8,251,916 B2 | 8/2012 | Speeg et al. |
| 8,454,531 B2 | 6/2013 | Speeg et al. |
| 8,480,595 B2* | 7/2013 | Speeg ............... A61B 10/0266 600/568 |
| 8,529,465 B2* | 9/2013 | Speeg ................ A61B 90/39 600/562 |
| 8,532,747 B2 | 9/2013 | Nock et al. |
| 8,568,333 B2 | 10/2013 | Hibner et al. |
| 8,622,924 B2 | 1/2014 | Speeg et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 9,486,186 B2 | 11/2016 | Fiebig et al. |
| 2005/0085838 A1* | 4/2005 | Thompson ......... A61B 10/0275 606/170 |
| 2005/0215921 A1* | 9/2005 | Hibner ............... A61B 10/0275 600/566 |
| 2006/0030785 A1* | 2/2006 | Field ...................... A61B 10/04 600/567 |
| 2006/0074345 A1 | 4/2006 | Hibner |
| 2006/0184063 A1* | 8/2006 | Miller ................. A61B 10/0266 600/568 |
| 2008/0146965 A1* | 6/2008 | Privitera ............ A61B 10/0266 600/567 |
| 2008/0195066 A1* | 8/2008 | Speeg ................ A61B 10/0275 604/326 |
| 2008/0281226 A1* | 11/2008 | Peters ................ A61B 10/0275 600/567 |
| 2009/0131816 A1* | 5/2009 | Ritchie .............. A61B 10/0283 600/563 |
| 2009/0131817 A1* | 5/2009 | Speeg ................ A61B 10/0275 600/564 |
| 2009/0131818 A1* | 5/2009 | Speeg ................ A61B 10/0266 600/564 |
| 2009/0131820 A1* | 5/2009 | Speeg ................ A61B 10/0275 600/566 |
| 2009/0131821 A1 | 5/2009 | Speeg et al. |
| 2009/0171242 A1* | 7/2009 | Hibner ............... A61B 10/0275 600/566 |
| 2009/0171243 A1* | 7/2009 | Hibner ............... A61B 10/0275 600/566 |
| 2009/0216152 A1* | 8/2009 | Speeg ................ A61B 10/0266 600/567 |
| 2009/0227893 A1* | 9/2009 | Coonahan .......... A61B 10/0283 600/566 |
| 2009/0264794 A1* | 10/2009 | Kodama ............ A61B 10/0233 600/567 |
| 2010/0152610 A1 | 6/2010 | Parihar et al. |
| 2010/0160815 A1* | 6/2010 | Parihar .............. A61B 10/0275 600/564 |
| 2010/0160819 A1 | 6/2010 | Parihar et al. |
| 2010/0292607 A1* | 11/2010 | Moore ............... A61B 10/0275 600/566 |
| 2010/0317995 A1* | 12/2010 | Hibner ............... A61B 10/0275 600/564 |
| 2011/0046513 A1* | 2/2011 | Hibner ............... A61B 10/0275 600/567 |
| 2011/0208090 A1 | 8/2011 | Parihar |
| 2012/0283563 A1* | 11/2012 | Moore ............... A61B 10/0096 600/437 |
| 2013/0079665 A1* | 3/2013 | Hibner ............... A61B 10/0275 600/567 |
| 2013/0144188 A1* | 6/2013 | Fiebig ................ A61B 10/0275 600/567 |
| 2013/0324882 A1 | 12/2013 | Mescher |
| 2014/0039343 A1* | 2/2014 | Mescher ............ A61B 10/0283 600/563 |
| 2014/0275999 A1* | 9/2014 | Speeg ................... A61B 10/02 600/424 |
| 2014/0336531 A1* | 11/2014 | Fiebig ................ A61B 10/0275 600/567 |
| 2015/0105690 A1* | 4/2015 | Hathaway .......... A61B 10/0275 600/566 |
| 2016/0081676 A1 | 3/2016 | Nock et al. |

OTHER PUBLICATIONS

U.S. Appl. No. 62/414,986, filed Oct. 31, 2016.
European Communication dated Apr. 24, 2017 for Application No. 16198672.4, 7 pages.
United Kingdom Intellectual Property Office Search Report dated Mar. 29, 2017 for Application No. GB1619242.9, 4 pages.

* cited by examiner

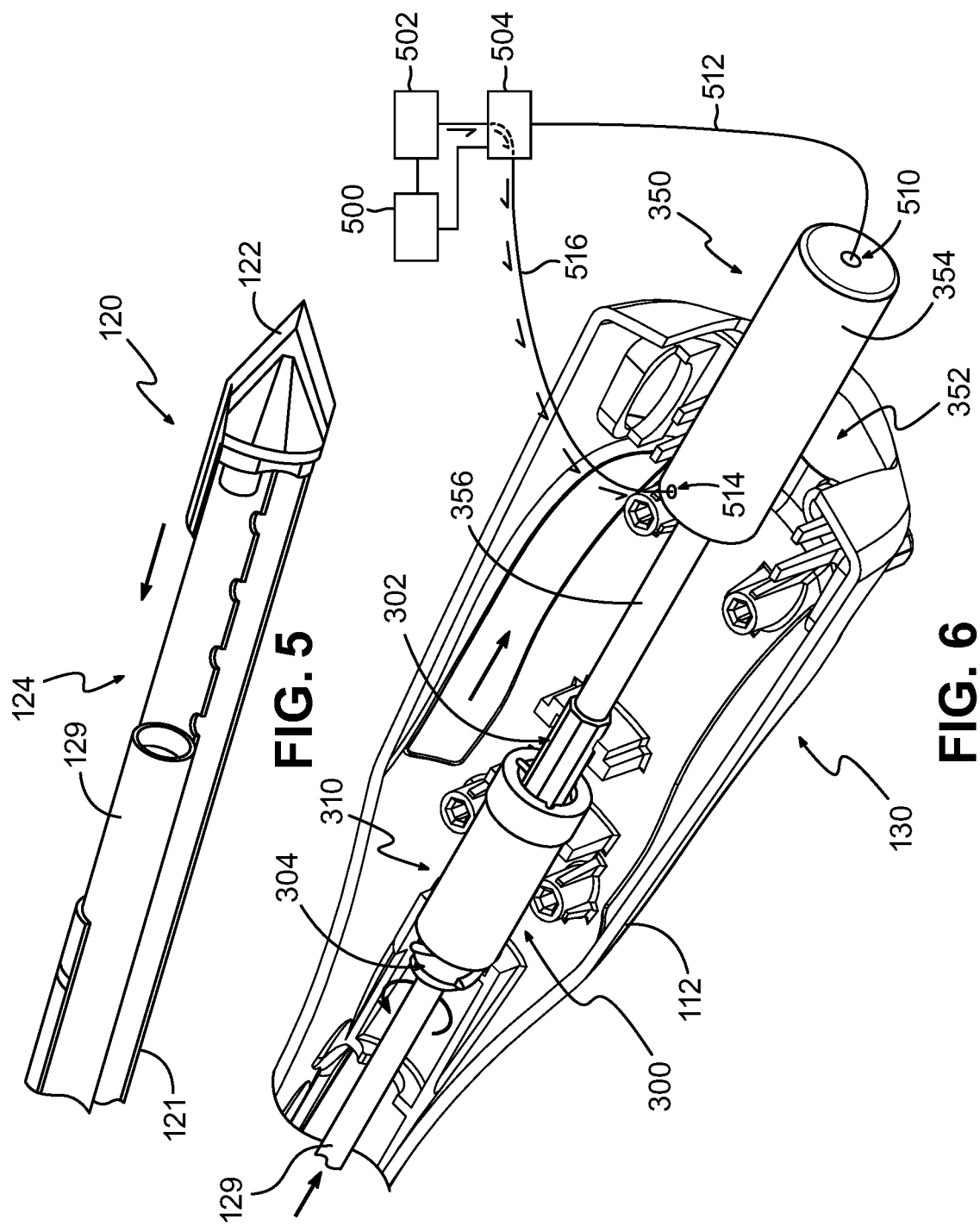

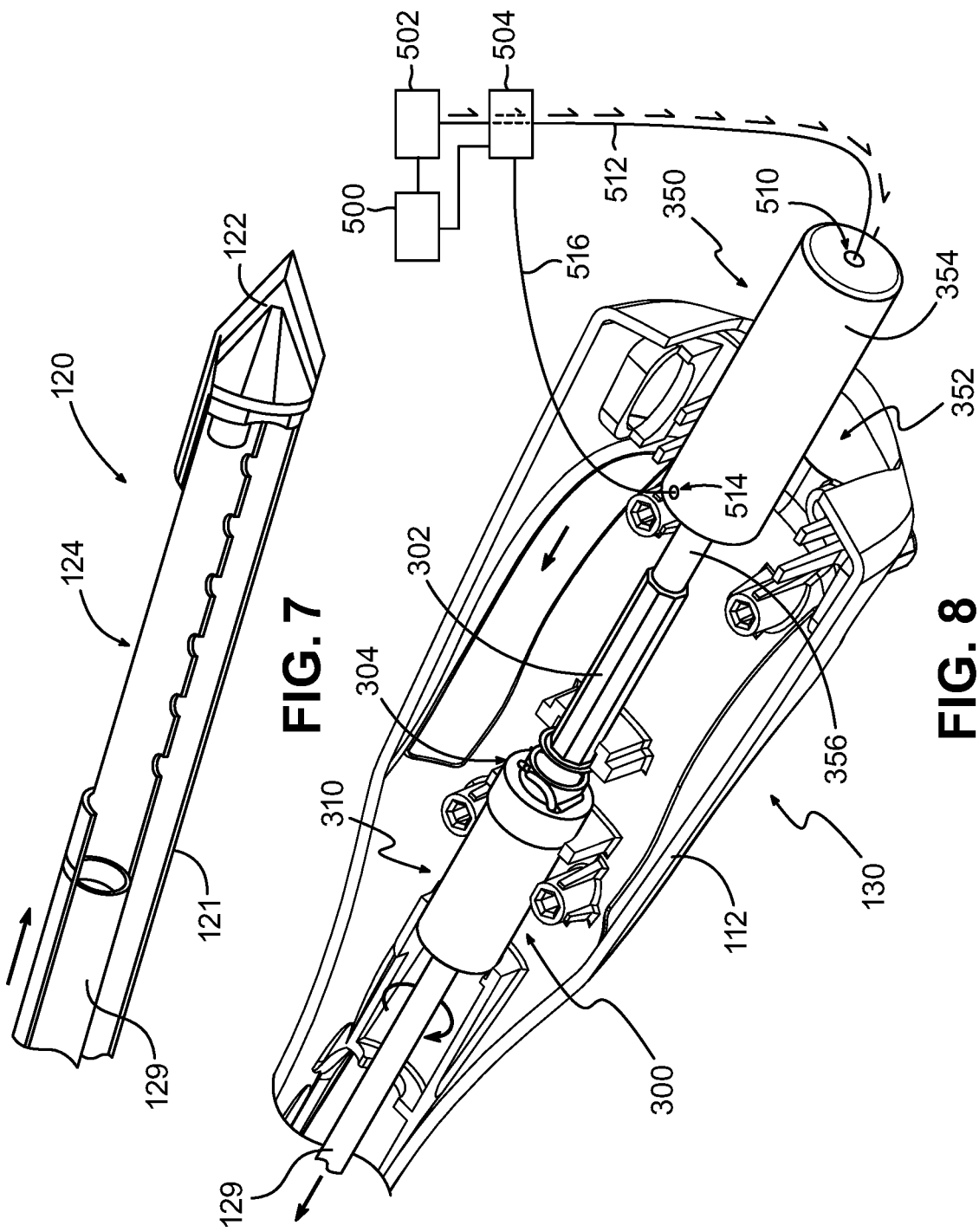

BIOPSY DEVICE WITH LINEAR ACTUATOR

PRIORITY

This application claims priority to U.S. Provisional Pat. App. No. 62/414,986, entitled "MRI Biopsy Device with MRI Compatible Linear Actuator," filed Oct. 31, 2016, the disclosure of which is incorporated by reference herein.

BACKGROUND

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Biopsy devices may be used under stereotactic guidance, ultrasound guidance, MRI guidance, Positron Emission Mammography ("PEM" guidance), Breast-Specific Gamma Imaging ("BSGI") guidance or otherwise.

An exemplary method for conducting a breast biopsy is to use a vacuum-assisted breast biopsy device. A current textbook in this area is "Vacuum-Assisted Breast Biopsy with Mammotome®", available Nov. 11, 2012, copyright 2013 by Devicor Medical Germany Gumby, published in Germany by Springer Medicine Verilog, Authors: Markus Hahn, Anne Tardyon and Jan Cassel man, ISBN 978-3-642-34270-7.

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Known biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatable Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tether less Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015 and U.S. Pat. No. 9,095,326, entitled "Biopsy System with Vacuum Control Module," issued Aug. 4, 2015. The disclosure of each of the above-cited U.S. patents is incorporated by reference herein.

Additional known biopsy devices and biopsy system components are disclosed in U.S. Pat. Pub. No. 2006/0074345, entitled "Biopsy Apparatus and Method," published Apr. 6, 2006 and now abandoned; U.S. Pat. Pub. No. 2008/0214955, entitled "Presentation of Biopsy Sample by Biopsy Device," published Sep. 4, 2008; U.S. Pat. Pub. No. 2009/0131821, entitled "Graphical User Interface for Biopsy System Control Module," published May 21, 2009, now abandoned; U.S. Pat. Pub. No. 2010/0152610, entitled "Hand Actuated Tether less Biopsy Device with Pistol Grip," published Jun. 17, 2010, now abandoned; U.S. Pat. Pub. No. 2010/0160819, entitled "Biopsy Device with Central Thumbwheel," published Jun. 24, 2010, now abandoned; U.S. Pat. Pub. No. 2013/0053724, entitled "Biopsy Device Tissue Sample Holder with Bulk Chamber and Pathology Chamber," published Feb. 28, 2013, will issue on May 3, 2016 as U.S. Pat. No. 9,326,755; U.S. Pat. Pub. No. 2013/0144188, entitled "Biopsy Device with Slide-In Probe," published Jun. 6, 2013; and U.S. Pat. Pub. No. 2013/0324882, entitled "Control for Biopsy Device," published Dec. 5, 2013. The disclosure of each of the above-cited U.S. patent application Publications, U.S. Non-Provisional patent applications, and U.S. Provisional patent applications is incorporated by reference herein.

A known localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removable receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

In U.S. Pat. Pub. No. 2005/0283069, entitled "MRI Biopsy Device Localization Fixture" published Dec. 22, 2005, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian position able guide for supporting and orienting an MRI-compatible biopsy instrument, and, in particular, a cannula/sleeve to a biopsy site of suspicious tissues or lesions. Another merely illustrative localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

In U.S. Pat. No. 7,831,290, issued Oct. 20, 2010, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a cannula/sleeve to a biopsy site of suspicious tissues or lesions.

A Z-stop may enhance accurate insertion, and prevent over-insertion or inadvertent retraction of a biopsy device targeting cannula/sleeve and obturator. In particular, a Z-stop may engage the localization fixture or cube at a distance from the patient set to restrict the depth of insertion of a biopsy device needle into a patient. Known Z-stop devices are disclosed in U.S. Pat. No. 7,507,210, entitled "Biopsy Cannula Adjustable Depth Stop," issued Mar. 24, 2009, the disclosure of which has been previously incorporated by reference herein.

When a biopsy procedure is performed under MRI guidance, it may be necessary to account for the presence of a strong magnetic field around MRI equipment significant during the procedure. For instance, during the procedure, devices that include ferrous materials may need to be removed from the procedure room during an imaging step. The necessity to remove devices from the procedure room during the imaging step produces additional steps, may increase cost, and may increase procedure time. Therefore, it may be desirable to reduce ferrous materials used in connection with breast biopsy procedures, particularly where MRI based guidance is used.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 5 depicts a partial perspective cross-sectional view of a needle assembly of the biopsy device of FIG. 1, with a cutter of the needle assembly in an intermediate longitudinal position during proximal travel from a distal position toward a proximal position;

FIG. 6 depicts still another perspective view of the cutter actuation assembly and the linear motor assembly of FIG. 2, with the cutter of the needle assembly in the intermediate longitudinal position of FIG. 5, and with the linear motor being actuated to drive the cutter toward the proximal position;

FIG. 7 depicts another partial perspective cross-sectional view of a needle assembly of FIG. 5, with the cutter of the needle assembly in the proximal position;

FIG. 8 depicts yet another perspective view of the cutter actuation assembly and the linear motor assembly of FIG. 2, with the cutter of the needle assembly in the proximal position of FIG. 7, and with the linear motor being actuated to drive the cutter toward the distal position;

Figure 1:
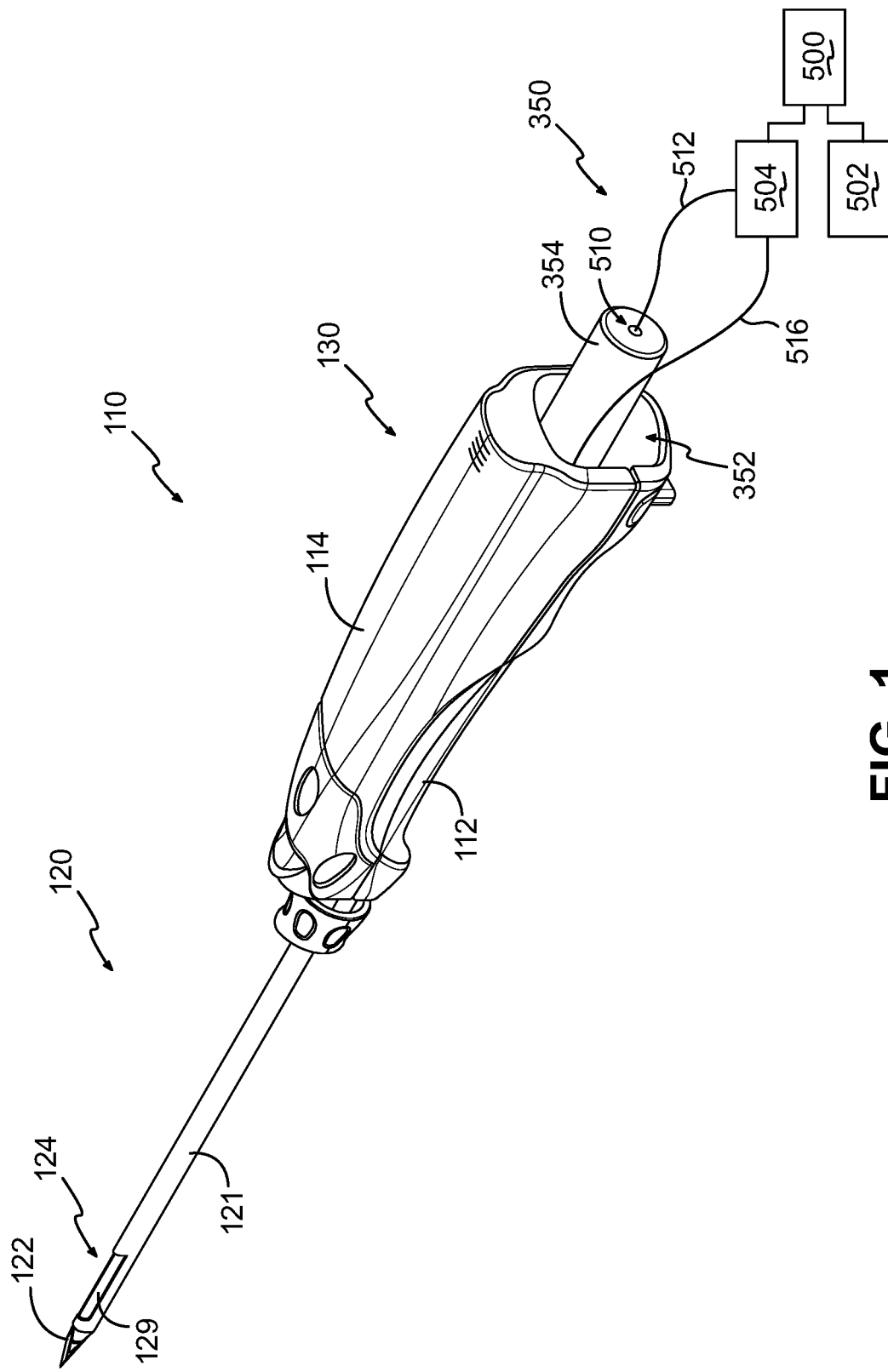
FIG. 1 depicts a perspective view of an exemplary biopsy device configured for use in MRI guided procedures.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

An apparatus for use with a biopsy device to promote Magnetic Resonance Imaging (MRI) compatibility is described and claimed. The apparatus includes a needle including a cutter and a lateral aperture, a cutter drive assembly, and a drive assembly. The drive assembly can be selectively removable from the biopsy device and in some versions a single MRI compatible rotary actuator is included to selectively drive the cutter via the cutter drive assembly. This reduces the amount of ferrous materials used in the biopsy device, thereby promoting MRI compatibility.

Figure 2:
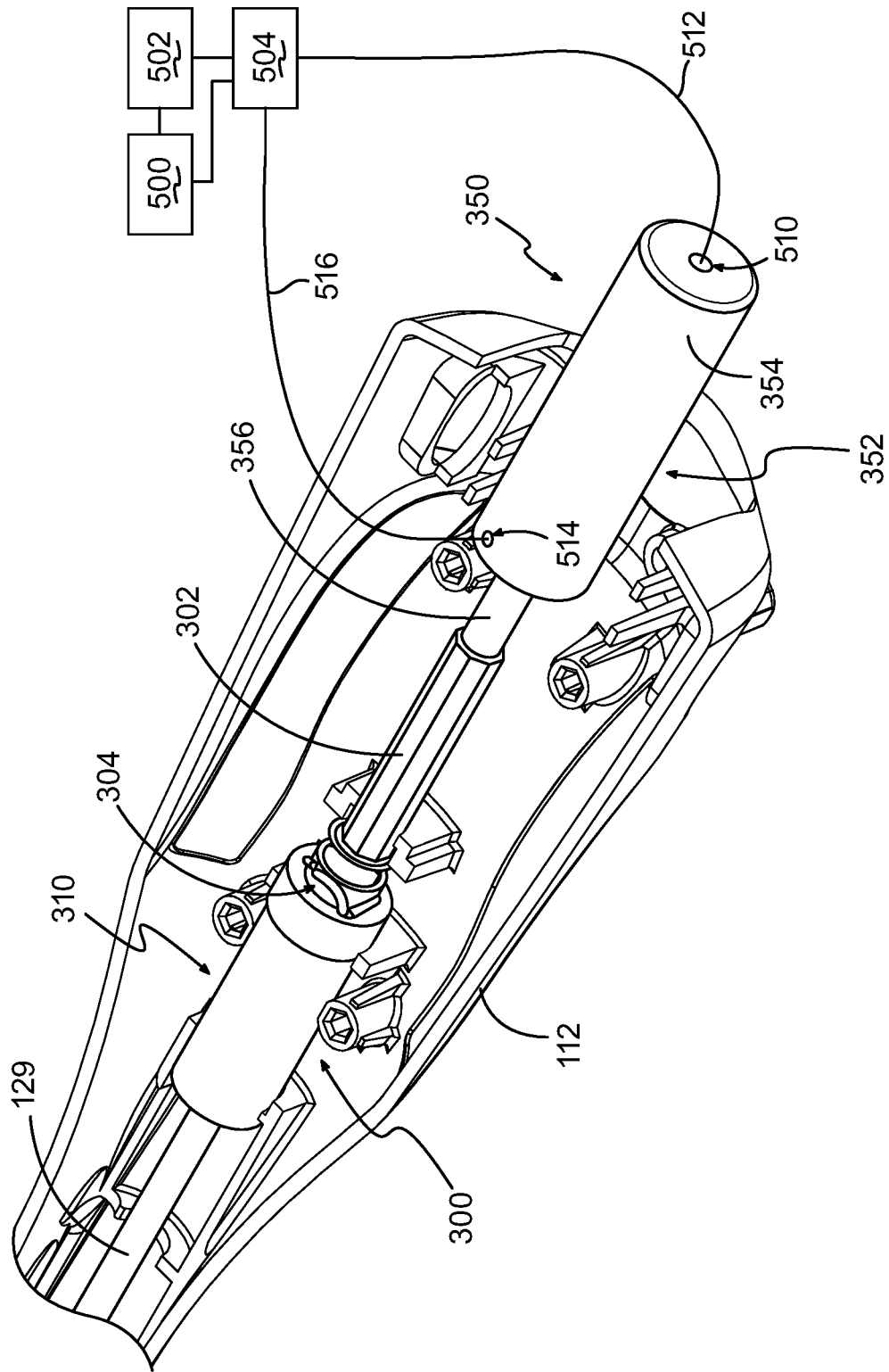
FIG. 2 depicts a perspective view of an exemplary cutter actuation assembly and linear motor assembly that may be readily incorporated into the biopsy device of FIG. 1.
Figure 3:
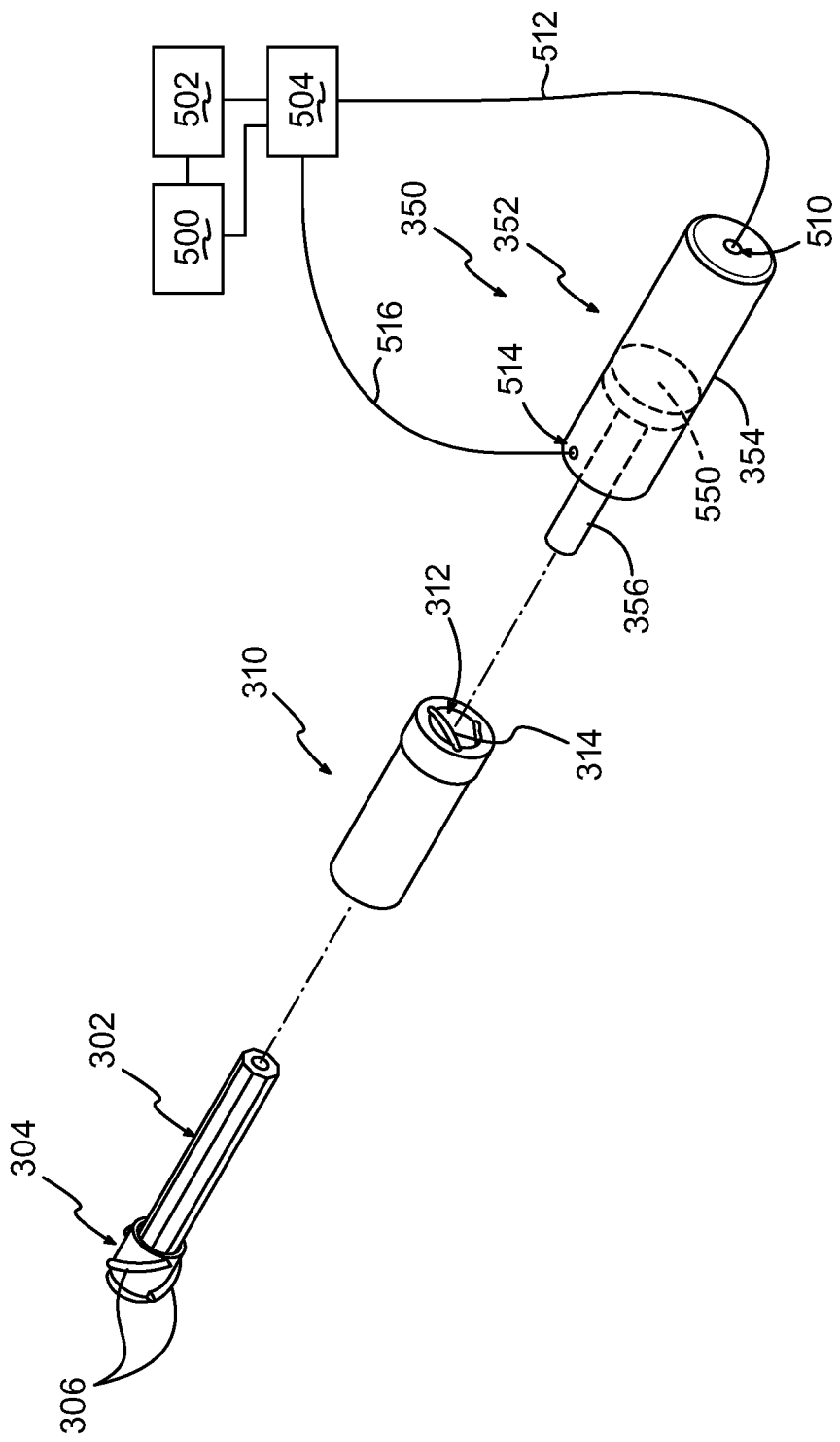
FIG. 3 depicts a perspective partially exploded view of the cutter actuation assembly and linear motor assembly of FIG. 2, with a portion of the linear motor assembly shown in phantom.
Figure 4:
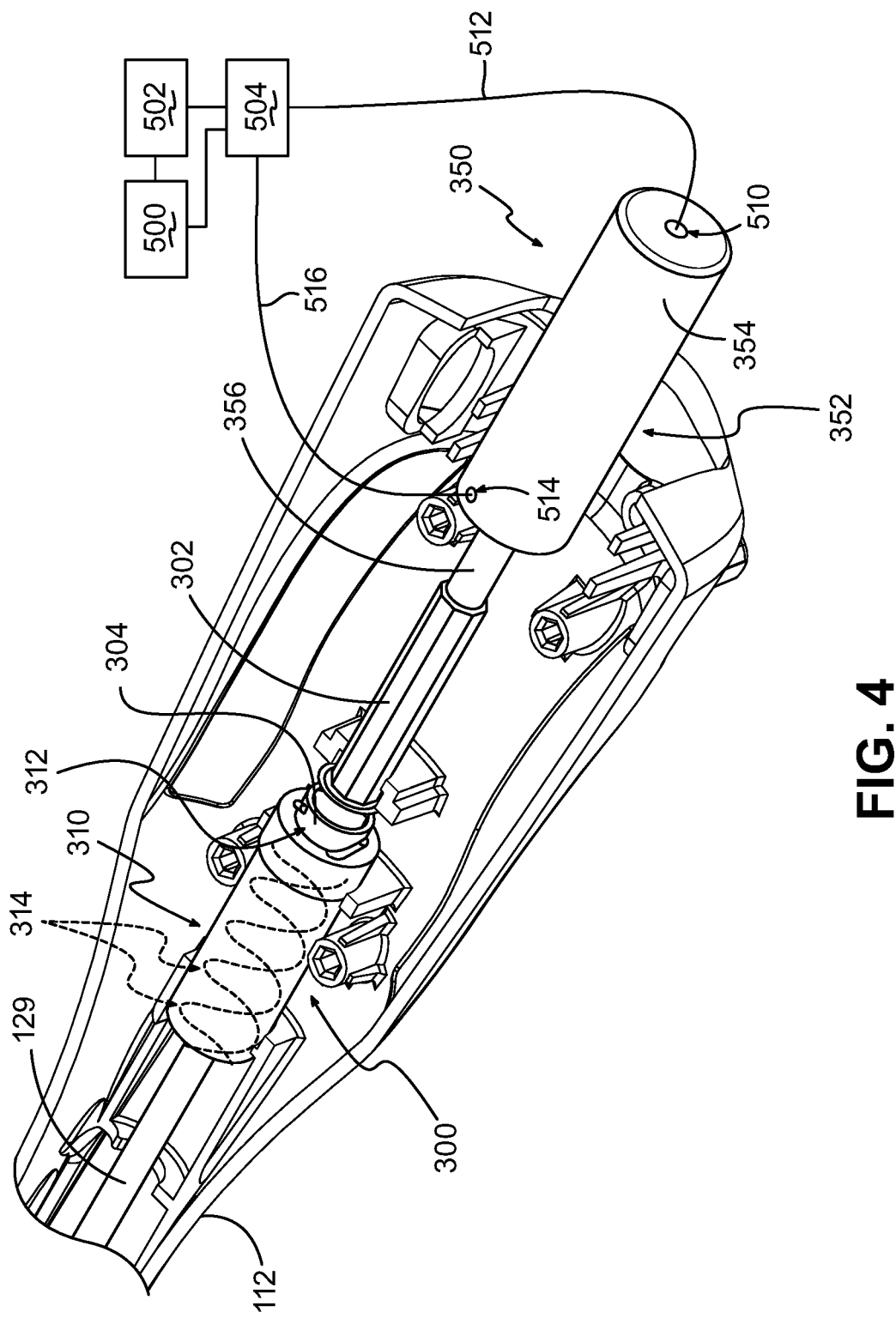
FIG. 4 depicts another perspective view of the cutter actuation assembly and the linear motor assembly of FIG. 2, with a portion of the cutter actuation assembly shown in phantom.

FIGS. 1-3 depict a biopsy device (110) for use in the collection of biopsy samples from the breast of a patient under Magnetic Resonance Imaging (MRI) assisted guidance. Biopsy device (110) of the present example is configured to be entirely MRI compatible. As will be described in greater detail below, biopsy device (10) is constructed to substantially eliminate all ferrous materials so as to not interfere with relatively strong magnetic fields that are generated by the MRI equipment. Although biopsy device (110) is described herein within the context of MRI based biopsy procedures, it should be understood that biopsy device (110) may be similarly used under various alternative forms of guidance such as stereotactic x-ray or ultrasonic guidance.

In the present example, biopsy device (110) is coupled with a control module (500), a pressurized fluid source (502), and a valve assembly (504). In addition, biopsy device (110) may be coupled with a vacuum source (not shown) and/or various other kinds of equipment such as a foot pedal, etc. In some versions, control module (500) is configured to operate biopsy device (110) on an automatic or semi-automatic basis through various predetermined operational modes. By way of example only, control module (500) may be configured and operable in accordance with at least some of the teachings of U.S. Pat. No. 6,752,768, entitled "Surgical Biopsy System with Remote Control for Selecting an Operational Mode," issued on Jun. 22, 2004, the disclosure of which is incorporated by reference herein; and/or U.S. Pat. No. 6,086,544, entitled "Control Apparatus for an Automated Surgical Biopsy Device," issued Jul. 11, 2000, the disclosure of which is incorporated by reference herein.

Additionally, in MRI based procedures biopsy device (110) may be used in connection with certain targeting features. For instance, a targeting feature may comprise a cannula and obturator based targeting set that is used in connection with a grid plate and guide cube to provide initial insertion and positioning within the breast of a patient. Biopsy device (110) is then inserted into the breast of a patient through cannula after removal of the obturator. By way of example only, such a cannula and obturator based targeting set may be configured and operable in accordance with at least some of the teachings of U.S. Pat. No. 8,568,333, entitled "Grid and Rotatable Cube Guide Localization Fixture for Biopsy Device," issued on Oct. 29, 2013, the disclosure of which is incorporated by reference herein; and/or U.S. Pat. Pub. No. 2016/0081676, entitled "MRI Biopsy System," published on Mar. 24, 2016, the disclosure of which is incorporated by reference herein.

As another merely illustrative example, biopsy device (110) may be used in connection with a pillar and post style targeting assembly. For instance, in an exemplary pillar and post targeting assembly, a post with a cradle is adjustably mounted to a post. The cradle along with the post are used to support biopsy device (110) and direct biopsy device (110) into the breast of a patient. The post is movable relative to the pillar to adjust the position of biopsy device (110) relative to a patient. Additionally, in some examples the pillar is also movable to adjust the positioning of biopsy device (110) relative to a patient. By way of example only, suitable pillar and post based targeting set may be configured and operable in accordance with at least some of the teachings of U.S. Pat. No. 7,708,751, entitled "MRI Biopsy Device," issued on May 4, 2010, the disclosure of which is incorporated by reference herein.

As is best seen in FIG. 1, biopsy device (110) comprises a needle assembly (120) a body (130), and a linear motor assembly (350). Needle assembly (120) extends distally from a distal portion of body (130), while linear motor assembly (350) extends proximally from a proximal portion of body (130). In some variations, linear motor assembly (350) is fully contained within body (130). Body (130) is sized and configured such that biopsy device (110) can be operated by a single hand of an operator. In particular, and as described in greater detail below, an operator may grasp body (130) with a single hand, insert needle assembly (120) into a patient's breast, all with a single hand. Alternatively, an operator can grasp body (130) with more than one hand and/or any desired assistance. In some settings, an operator can capture a plurality of tissue samples with a single insertion of needle assembly (120) into the patient's breast. Such tissue samples can be pneumatically deposited in a tissue sample holder or other structure and then later retrieved for analysis. Various examples of tissue sample holders that may be incorporated into biopsy device (110) or otherwise associated with biopsy device (110) are described in various references cited herein; while other suitable examples will be apparent to those of ordinary skill in the art in view of the teachings herein.

Body (130) of the present example comprises a probe (112) and a holster (114). Although not shown, it should be understood that probe (112) is generally separable from holster (114). For instance, probe (112) and holster (114) can be removably coupled using bayonet mounts or any other suitable structure. By way of example only, probe (112) and holster (114) of the present example may be configured and operable in accordance with at least some of the teachings of U.S. Pat. No. 8,177,728, entitled "Valve Mechanism for Tetherless Biopsy Device," issued on Oct. 29, 2013, the disclosure of which is incorporated by reference herein.

Needle assembly (120) of the present example comprises a cannula (121) with a piercing tip (122) and a lateral aperture (124). Tissue piercing tip (122) is configured to pierce and penetrate tissue, without requiring a high amount of force, and without requiring an opening to be pre-formed in the tissue prior to insertion of tip (122). A cutter (129) is disposed in a cutter-receiving lumen (not shown) defined by cannula (121), and is operable to rotate and translate within the cutter-receiving lumen of cannula (121) as will be described in greater detail below. Lateral aperture (124) is located proximal to tip (122), is in fluid communication with the cutter-receiving lumen, and is configured to receive tissue when needle (120) is inserted in a breast and when a cutter (129) is retracted as will also be described in greater detail below. By way of example only, needle assembly (120) of the present example may be configured and operable in accordance with at least some of the teachings of U.S. Pat. No. 8,177,728, entitled "Valve Mechanism for Tetherless Biopsy Device," issued on May 15, 2012, the disclosure of which is incorporated by reference herein; and/or U.S. Pat. No. 7,918,804, entitled "Biopsy Device with Vacuum Assisted Bleeding Control," issued on Apr. 5, 2011, the disclosure of which is incorporated by reference herein.

Although not shown, in some versions a venting valve assembly or other suitable valving feature may be coupled with needle assembly (120) to selectively apply atmospheric venting and/or other changes in pneumatic state to needle assembly (120). Some such valve assemblies may be coupled with cutter (129), with cutter actuation assembly (300), and/or with linear motor actuation assembly (350). In some of these examples, the venting valve assembly may be located on-board in body (130); and cutter (129), cutter actuation assembly (300), and/or linear motor actuation assembly (350) may be configured to actuate the valve assembly of needle assembly (120) to transition needle assembly (120) between two or more pneumatic states. Alternatively, in some examples, the on-board venting valve assembly for needle assembly (120) is omitted entirely and the pneumatic state of needle assembly (120) is controlled externally.

FIGS. 2 and 3 show an exemplary cutter actuation assembly (300) and linear motor assembly (350) incorporated into biopsy device (110). Cutter actuation assembly (300) is generally configured to be linearly actuated to simultaneously translate and rotate cutter (129). As will be described in greater detail below, cutter (129) is translated longitudinally by linear motor assembly (350), and cutter actuation assembly (300) is responsive to the translation of cutter (129) to rotate cutter (129) as cutter (129) is translated longitudinally. Cutter actuation assembly comprises a cutter sleeve (302) fixedly secured to the exterior of cutter (129). Because cutter sleeve (302) is unitarily secured to cutter (129) in this example, translation or rotation of cutter (129) also results in corresponding translation or rotation of cutter sleeve (302) and vice versa.

Cutter sleeve (302) includes an integral rotation member (304) with threading (306) extending outwardly from rotation member (304). As will be described in greater detail below, threading (306) is configured to drive rotation of rotation member (304), cutter sleeve (302) and cutter (129) into rotation in response to translation of cutter (129).

Cutter actuation assembly (300) further includes a receiving member (310). Receiving member (310) is fixedly secured to body (130) such that receiving member (310) remains stationary as cutter (129) is rotated and translated. Receiving member (310) has a generally cylindrical shape with a bore (312) extending longitudinally through receiving member (310). Bore (312) is configured to coaxially receive cutter (129) and rotation member (304) of cutter sleeve (302). Extending inwardly into bore (312), receiving member (310) further includes threading (314) that is configured to engage threading (306) of rotation member (304). As will be described in greater detail below, threading (314) of receiving member (310) engages threading (306) of rotation member (304) as cutter (129) is translated. Threading (314) of receiving member (310) then causes cutter (129) to rotate via threading (306) of rotation member (304). Receiving member (310) thus serves as a nut in this example; while rotation member (304) serves as a lead screw in this example. In some other versions, different kinds of structures may be incorporated into cutter actuation assembly (300) to convert longitudinal motion of cutter (129) into combined longitudinal and rotational motion of cutter (129). Various alternative kinds of structures that may be used to provide such combined motion will be apparent to those of ordinary skill in the art in view of the teachings herein.

Linear motor assembly (350) of the present example is configured to be selectively removable from biopsy device (110) such that an operator may selectively choose a suitable linear motor assembly (350) that may be appropriate for a given procedure. Although not shown, it should be understood that linear motor assembly (350) can include numerous structural features configured to promote removability of linear motor assembly (350) from biopsy device (110). By way of example only, suitable features may include snap fitting fasteners, complementary housings, hinged doors, linear sliders, detents, etc.

Linear motor assembly (350) of the present example comprises a linear actuator (352). As used herein, the term "linear actuator" should not be read to include any kind of rotary motor. In other words, rotary motors should be deemed excluded from the definition of the term "linear actuator." Linear actuator (352) of the present example is configured as a non-ferrous MRI compatible pneumatic cylinder. In some other examples, linear actuator (352) comprises a variety of other alternative devices such as hydraulic cylinders, self-contained lead screw based linear actuators, solenoids, etc. As similarly discussed above with respect to linear motor assembly (250), several alternative linear motor assemblies (350) may be included with biopsy device (110) with each linear motor assembly (350) being equipped with a different style of linear actuator (352). A selected linear motor assembly (350) may then be used with biopsy device (110) depending on the type of imaging guidance being used.

Regardless of the particular configuration of linear motor assembly (350), linear actuator (352) of the present example includes a cylinder (354) and an actuation rod (356). Actuation rod (356) extends distally from cylinder (354) and is coupled directly to cutter (129). As will be described in greater detail below, actuation rod (356) is translatable relative to cylinder (354) to translate cutter (129). Although not shown, it should be understood that in some examples, linear actuator (352) is configured with a bore extending longitudinally through cylinder (354) and actuation rod (356). In such examples, the bore is included to permit cutter (129) to extend entirely through linear actuator (352) to permit cutter (129) to communicate tissue samples with a tissue sample holder or other tissue receiving structure that is located proximal to linear motor assembly (350). Various suitable ways in which cutter (129) may pass through linear motor assembly (350) to communicate tissue samples with a tissue sample holder or other tissue receiving structure that is located proximal to linear motor assembly (350), while still being linearly translated by linear motor assembly (350), and while still being rotatable relative to linear motor assembly (350), will be apparent to those of ordinary skill in the art in view of the teachings herein.

As noted above, linear motor assembly (350) may take a variety of forms and may be actuated in various kinds of ways. In the present example, for illustrative purposes only, linear motor assembly (350) is actuated by pressurized fluid (e.g., pressurized air, etc.). To that end, and as best shown in FIG. 3, the proximal end of actuation rod (356) is secured to a piston (550), which is slidably disposed within cylinder (354). Cylinder (354) defines a proximal port (510) that is located proximal to piston (550); and a distal port (514) that is located distal to piston (550). Valve assembly (504) is in fluid communication with proximal port (510) via a first conduit (512); and with distal port (514) via a second conduit (516).

Pressurized fluid source (502) is in fluid communication with valve assembly (504) and is thereby operable to deliver pressurized fluid to valve assembly (504). By way of example only, pressurized fluid source (502) may comprise a pump and/or a vessel containing a predetermined volume of pre-pressurized fluid.

Control module (500) is communicatively coupled with pressurized fluid source (502) and valve assembly (504). In particular, control module (500) is operable to selectively activate pressurized fluid source (502). Such activation may be carried out in response to an operator input, automatically based on a control algorithm, and/or on any other kind of basis. Control module (500) is further operable to selectively activate valve assembly (504) to direct pressurized fluid from pressurized fluid source (502) to either proximal port (510) via first conduit (512) or distal port (514) via second conduit (516). In some versions, valve assembly (504) is further configured to vent distal port (514) to atmosphere when pressurized fluid is being communicated to proximal port (510); and vent proximal port (510) to atmosphere when pressurized fluid is being communicated to distal port (514).

Control module (500) may activate valve assembly (504) to transition between the above-noted states (among others) based on any suitable kind of input. By way of example only, control module (500) may activate valve assembly (504) to transition between the above-noted states based on operator input and/or based on a control algorithm.

In versions where control module (500) activates valve assembly (504) to transition between the above-noted states based on a control algorithm, various kinds of data inputs may be processed in such a control algorithm. For instance, control module (500) may include a timer (not shown); and control module (500) may automatically change the state of valve assembly (504) based on the passage of a certain amount of time after the occurrence of a certain event (e.g., after an operator has activated a button or other input). In addition, or in the alternative, biopsy device (110) may include a sensor (not shown) that is configured to detect the longitudinal position of cutter (129). The sensor may be in communication with control module (500), such that control module automatically changes the state of valve assembly (504) based on cutter (129) reaches a certain position. For instance, control module (500) may automatically activate valve assembly (504) to direct pressurized fluid to proximal port (510) when the sensor detects cutter (129) reaching a proximal position after travelling proximally from a distal position; and/or automatically activate valve assembly (504) to direct pressurized fluid to distal port (514) when the sensor detects cutter (129) reaching a distal position after travelling distally from a proximal position. Other suitable ways in which control module (500) may automatically activate valve assembly (504) will be apparent to those of ordinary skill in the art in view of the teachings herein.

FIGS. 5-8 show an exemplary use of cutter actuation assembly (300) and linear motor assembly (350) to sever a biopsy sample. In such a use of cutter actuation assembly (300) and linear motor assembly (350), cutter (129) begins in a distal position such that the distal end of cutter (129) is positioned to close lateral aperture (124). Cutter (129) is then retracted as shown in FIG. 5 by retracting actuation rod (356) of linear actuator (352) into cylinder (354) as shown in FIG. 6. This is accomplished by valve assembly (504) directing pressurized fluid to distal port (514), such that the pressurized fluid impinges against the distal face of piston (550) to drive piston (550), actuation rod (356), and cutter (129) proximally. As cutter (129) is retracting, threading (306) of rotation member (304) engages threading (314) of receiving member (310). This causes rotation member (304) to rotate. Because receiving member (310) is integral with cutter sleeve (302), which is fixedly secured to cutter (129), rotation of receiving member (310) results in corresponding rotation of cutter (129). Thus, as cutter (129) is translated proximally, cutter (129) simultaneously rotates via receiving member (310) and rotation member (304).

Cutter (129) is retracted relative to lateral aperture (124) until cutter (129) is positioned in an open position, where the distal end of cutter (129) is disposed proximally of lateral aperture (124) as shown in FIG. 7. At this stage, vacuum may be applied to cannula (121) and/or cutter (129) to prolapse tissue into lateral aperture (124). Once tissue is prolapsed within lateral aperture (124), cutter (129) can be advanced to sever a tissue sample. To advance cutter (129) actuation rod (356) is advanced. This is accomplished by valve assembly (504) directing pressurized fluid to proximal port (510), such that the pressurized fluid impinges against the proximal face of piston (550) to drive piston (550), actuation rod (356), and cutter (129) distally. As cutter (129) is advanced, threading (306) of rotation member (304) engages threading (314) of receiving member (310), thereby simultaneously translating and rotating cutter (129). As cutter (129) advances distally past lateral aperture (124), cutter (129) severs a tissue sample from the tissue sample prolapsed through lateral aperture (124).

Once actuation rod (356) is fully advanced and cutter (129) has severed the tissue sample, cutter (129) may be reciprocated again to obtain one or more additional tissue samples. Regardless of the number of cutter (129) strokes, the severed tissue sample(s) may be collected using a tissue sample holder or other tissue collection structure as described above. The same process may be repeated any suitable number of times to collect a desired number of tissue samples. The tissue sample collection structure can be any known tissue sample collection structure that is suitable to collect tissue during a vacuum assisted breast biopsy (VABB), including but not limited to the various kinds of tissue sample collection structures described in various references that are cited herein.

Figure 9:
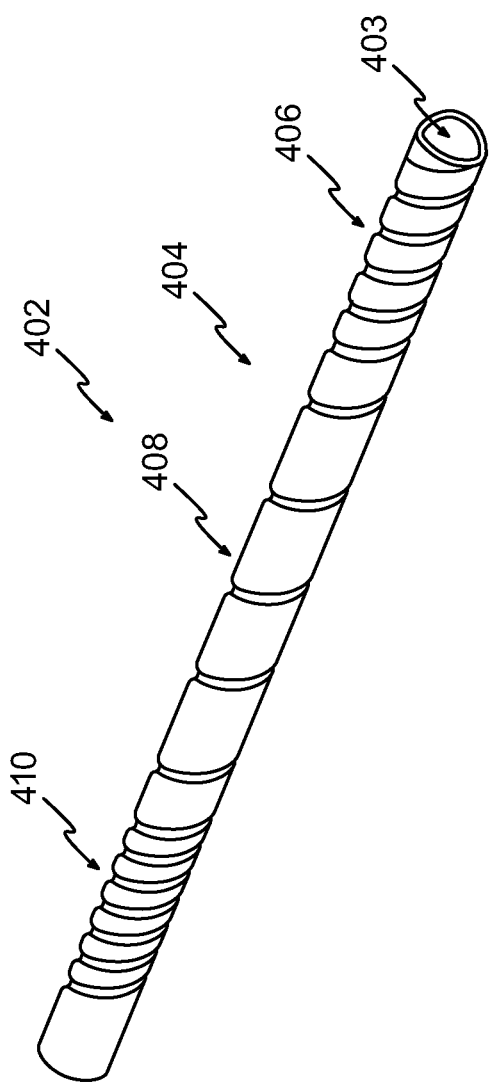
FIG. 9 depicts a perspective view of an exemplary alternative cutter sleeve that may be readily incorporated into the cutter actuation assembly of FIG. 2.

FIG. 9 shows an exemplary alternative cutter sleeve (402) that may be readily incorporated into cutter actuation assembly (300) described above in lieu of cutter sleeve (302). Cutter sleeve (402) of the present example is generally operable as described above with respect to cutter sleeve (302). For instance, cutter sleeve (402) is generally hollow and includes a bore (403), which permits at least a portion of cutter (129) to be received within the hollow interior of cutter sleeve (402). Additionally, cutter sleeve (402) includes threads (404), which are configured to engage threading (314) of receiving member (310) to initiate rotation of cutter sleeve (402), and cutter (129) via cutter sleeve (402) in response to translation of cutter sleeve (402). To the extent that at least a portion of cutter sleeve (402) appears to have a triangular or rounded triangular cross-sectional profile in FIG. 9, it should be understood that cutter sleeve (402) may have a circular cross-sectional profile along the full length of cutter sleeve (402).

Unlike cutter sleeve (302) described above, cutter sleeve (402) includes three pitched regions (406, 408, 410) having variable pitch. In particular, cutter sleeve (402) comprise a first pitched region (406), a second pitched region (408) and a third pitched region (410). Generally, threading (404) has a generally fine pitch in first pitched region (406) and second pitched region (410). By contrast, in second pitched region (408), threading (404) is relatively course. In some instances, variable pitch of threading (404) may be desirable to provide variable translation speed of cutter (129) as cutter (129) is actuated through a cutting stroke. In the present example, cutter sleeve (402) would be used with a variation of receiving member (310) where a simple pin or other boss structure is substituted for threading (314), allowing the pin or other boss structure to traverse all pitch regions (406, 408, 410) without causing binding or interference. As the pin or other boss structure of the alternative receiving member encounters a different pitch region (406, 408, 410), this will result in a different translation rate of cutter sleeve (402) and cutter (129) by providing more or less resistance to linear motor assembly (350) depending on the pitch encountered by the pin or other boss structure of the alternative receiving member.

Although pitched regions (406, 408, 410) are shown in the present example as having specific pitches, it should be understood that in other examples that particular pitch used may be altered as desired. Additionally, while pitched regions (406, 408, 410) follow a particular pattern of pitch in the present example (e.g., fine-course-fine), it should be understood that in other examples various alternative patterns may be used. For instance, the pitch pattern may instead be coarse-fine-course.

Figure 10A:
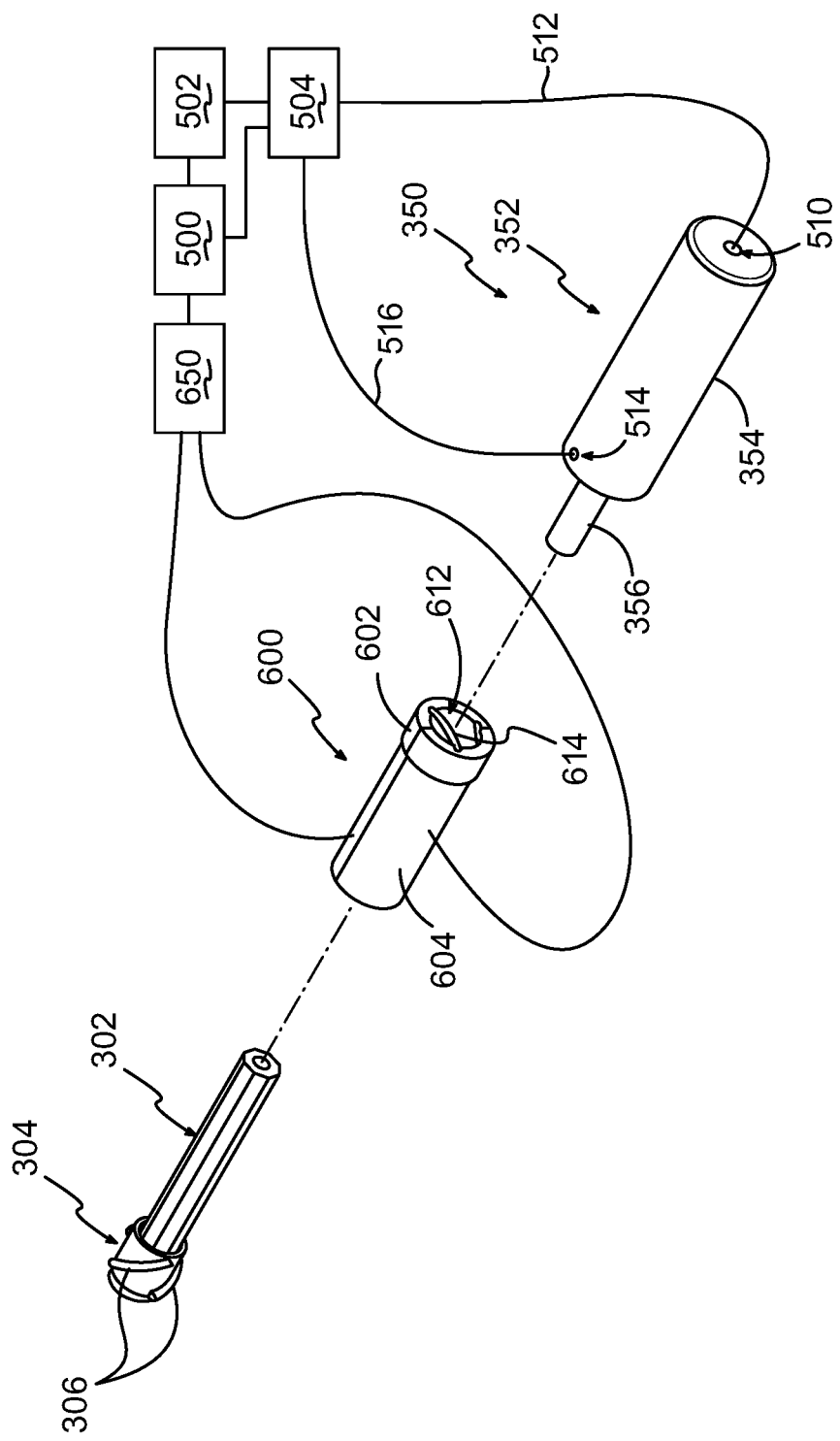
FIG. 10A depicts a perspective partially exploded view of an exemplary alternative cutter actuation assembly and linear motor assembly, with a portion of the linear motor assembly shown in phantom, and with a split nut of the cutter actuation assembly shown in a joined state.
Figure 10B:
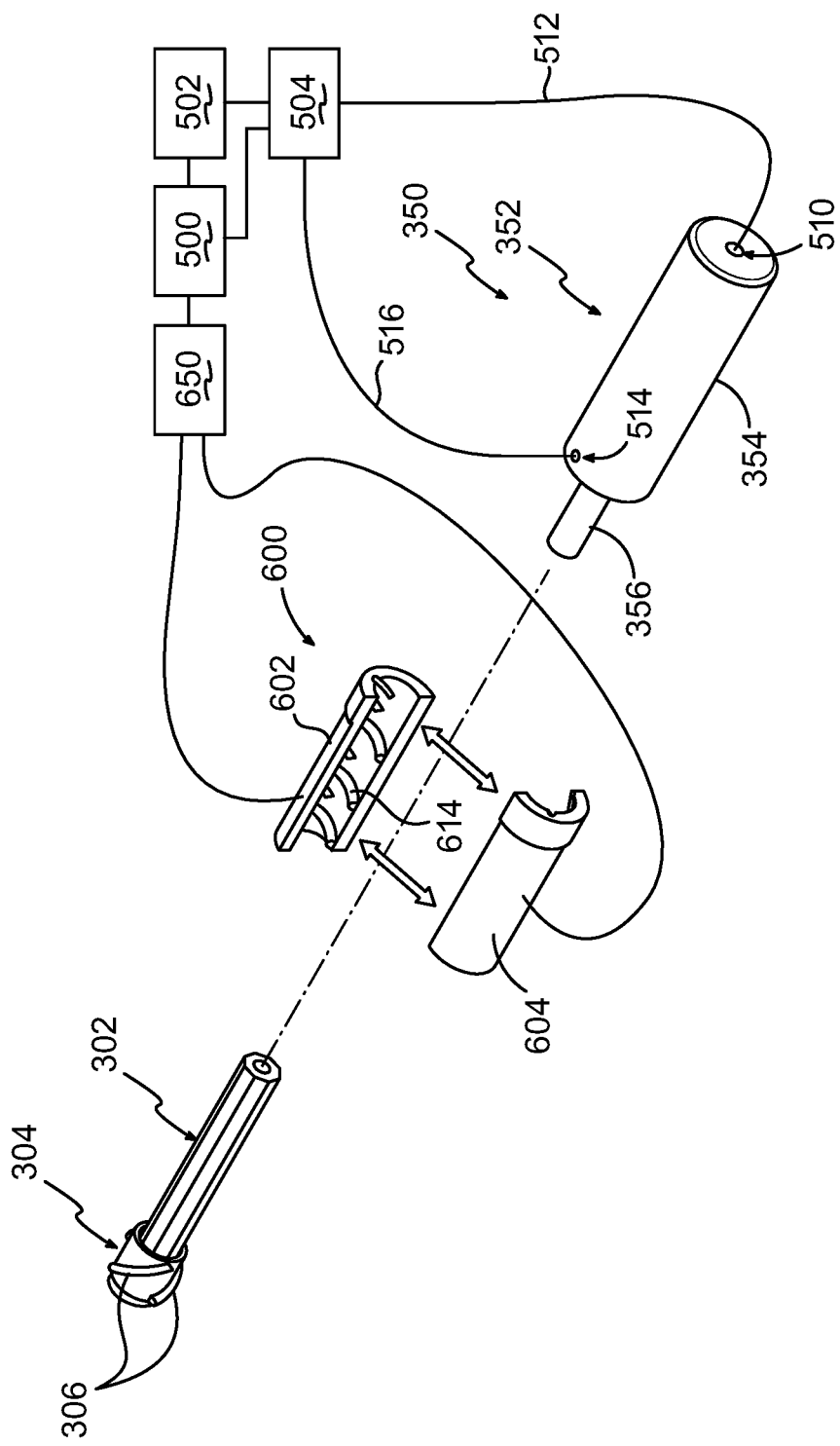
FIG. 10B depicts a perspective partially exploded view of the cutter actuation assembly and linear motor assembly of FIG. 10A, with a portion of the linear motor assembly shown in phantom, and with the split nut shown in a separated state.

FIGS. 10A-10B show another exemplary variation of receiving member (310). In particular, FIGS. 10A-10B show a receiving member (600) that includes a first half (602) and a second half (604). Halves (602, 604) are longitudinally coextensive and laterally separable in this example. When halves (602, 604) are joined together, as shown in FIG. 10A, halves (602, 604) cooperate to define a bore (612) that coaxially receives cutter (129) and rotation member (304) of cutter sleeve (302). Each half (602, 604) also defines a complementary threading (614) that is configured to interact with threading (306) of rotation member (304), just like threading (314) interacts with threading (306) of rotation member (304) as described above. Thus, when halves (602, 604) are joined together, as shown in FIG. 10A, receiving member (600) of the present example behaves identically to receiving member (310) as described above.

Probe (112) may include bosses, channels, and/or other structural features that are configured to support and guide halves (602, 604) as halves (602, 604) transition between the joined state (FIG. 10A) and the separated state (FIG. 10B). Such structural features may ensure that halves (602, 604) join together in a consistent, reliable fashion to ensure that threading (614) will successfully mesh with threading (306). Various suitable structures that may be used to support and guide halves (602, 604) will be apparent to those of ordinary skill in the art in view of the teachings herein.

An actuator (650) is coupled with halves (602, 604) and is operable to selectively drive halves (602, 604) toward and away from each other, such that actuator (650) is operable to transition halves (602, 604) between the joined state (FIG. 10A) and the separated state (FIG. 10B). In some other versions, halves (602, 604) are resiliently biased or otherwise biased to assume the joined state (FIG. 10A); and actuator (650) is operable to selectively drive halves (602, 604) apart to reach and maintain the separated state (FIG. 10B). In still other versions, halves (602, 604) are resiliently biased or otherwise biased to assume the separated state (FIG. 10B); and actuator (650) is operable to selectively drive halves (602, 604) toward each other to reach and maintain the joined state (FIG. 10A).

In operation, actuator (650) is configured to provide halves (602, 604) in the joined state (FIG. 10A) as cutter (129) is driven distally, such that cutter (129) will rotate while translating distally. In the present example, actuator (650) is further configured to provide halves (602, 604) in the separated state (FIG. 10B) as cutter (129) is driven proximally, such that cutter (129) will not rotate while translating proximally.

Actuator (650) may take a variety of forms. For instance, actuator (650) may comprise a mechanical device that is actuated by cutter sleeve (302) or some other feature that is secured by cutter (129), such that actuator (650) is automatically activated in a purely mechanical based on the longitudinal position of cutter (129). By way of example only, cutter sleeve (302) may actuate a trip mechanism and/or cam assembly, etc. when cutter (129) reaches a distal position and/or when cutter (129) reaches a proximal position, thereby activating actuator (650) to change the state of receiving member (600). Various suitable components and configurations that may be used to provide a purely mechanical actuation of actuator (650) will be apparent to those of ordinary skill in the art in view of the teachings herein.

As another merely illustrative example, actuator (650) may be activated electronically. For instance, a sensor (not shown) may be configured to detect the longitudinal position of cutter (129). Actuator (650) may be in communication with this sensor, such that actuator (650) automatically changes the state of receiving member (600) based on the longitudinal position of cutter (129). As yet another merely illustrative example, actuator (650) may be in communication with control module (500), such that control module (500) may activate actuator (650), based on a control algorithm or otherwise. For instance, the same condition(s) that cause(s) control module (500) to change the state of valve assembly (504) may also cause control module (500) to activate actuator (650) and thereby change the state of receiving member (600). Thus, receiving member (600) and valve assembly (504) may change states simultaneously, in response to control module (500) or otherwise. Other suitable ways in which actuator (650) may be activated electronically will be apparent to those of ordinary skill in the art in view of the teachings herein.

While the examples described above include an internal threading (314, 614), some variations may include some other kind of structure instead of threading (314, 614). For instance, threading (314, 614) may be replaced with a pin, some other kind of boss structure, or any other suitable kind of structure as will be apparent to those of ordinary skill in the art in view of the teachings herein.

As yet another merely illustrative example, receiving member (600) may be at least partially configured and operable like a split nut assembly as described in U.S. Pub. No. 2011/02008090, entitled "Spring Loaded Biopsy Device," published Aug. 25, 2011, the disclosure of which is incorporated by reference herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a cannula extending distally from the body, the cannula including:
      (i) a distal end, and
      (ii) a lateral aperture located proximal to the distal end;
   (c) a cutter positioned within the cannula and configured to sever tissue protruding through the lateral aperture;
   (d) a cutter rotation member unitarily secured to the cutter and configured to translate and rotate unitarily with the cutter;
   (e) a receiving member associated with the body and positioned coaxially about the cutter, the receiving member being configured to cooperate with the cutter rotation member to drive rotation of the cutter in response to longitudinal motion of the cutter; and
   (f) a linear actuator having a body and a rod, the rod being configured to translate along an axis relative to the body, the rod being further configured to drive motion of the cutter while permitting rotary motion of the cutter via engagement between the cutter rotation member and the receiving member.

2. The apparatus of claim 1, the cutter rotation member including a sleeve coaxially positioned about the cutter.

3. The apparatus of claim 2, the receiving member including a cylindraceous member coaxially disposed about the sleeve.

4. The apparatus of claim 1, the cutter rotation member including a first threading, the receiving member is configured to engage the first threading to thereby rotate the cutter rotation member in response to longitudinal motion of the cutter rotation member.

5. The apparatus of claim 4, the receiving member including a second threading configured to mesh with the first threading.

6. The apparatus of claim 1, the linear actuator including a pneumatic cylinder.

7. The apparatus of claim 6, the linear actuator further including a piston slidably disposed in the pneumatic cylinder.

8. The apparatus of claim 7, the piston being secured to the cutter via the rod, the piston being configured to drive longitudinal motion of the cutter while permitting rotary motion of the cutter.

9. The apparatus of claim 7, the pneumatic cylinder including a proximal port, the proximal port being configured to communicate pressurized fluid to a proximal face of the piston to thereby drive the piston and cutter distally.

10. The apparatus of claim 7, the pneumatic cylinder including a distal port, the distal port being configured to communicate pressurized fluid to a distal face of the piston to thereby drive the piston and cutter proximally.

11. The apparatus of claim 7, the pneumatic cylinder including:
   (i) a proximal port configured to communicate pressurized fluid to a proximal face of the piston to thereby drive the piston and cutter distally, and
   (ii) a distal port configured to communicate pressurized fluid to a distal face of the piston to thereby drive the piston and cutter proximally.

12. The apparatus of claim 11, further comprising a valve assembly configured to selectively direct pressurized fluid to a selected one of the proximal port or the distal port.

13. The apparatus of claim 12, the valve assembly being further configured to vent the distal port to atmosphere when communicating pressurized fluid to the proximal port, the valve assembly being further configured to vent the proximal port to atmosphere when communicating pressurized fluid to the distal port.

14. The apparatus of claim 12, further comprising:
   (a) a control module operable to activate the valve assembly; and
   (b) a pressurized fluid source the control module being further operable to activate the pressurized fluid source.

15. The apparatus of claim 1, the receiving member being configured to remain engaged with the cutter rotation member during proximal motion of the cutter to thereby drive rotation of the cutter while the cutter travels from a distal position toward a proximal position.

16. The apparatus of claim 1, the linear actuator comprising a solenoid.

17. The apparatus of claim 1, the receiving member including:
   (i) a first portion, and
   (ii) a second portion,
   the first and second portions being configured move laterally relative to each other to thereby transition between a joined state and a separated state,
   the first portion and the second portion being configured to engage the cutter rotation member when the first portion and the second portion are in the joined state,
   the first portion and the second portion being configured to not engage the cutter rotation member when the first portion and the second portion are in the separated state.

18. The apparatus of claim 17, further comprising a drive member actuator, the drive member actuator being operable to transition the first and second portions of the receiving member between the joined and separated states, based on the longitudinal position of the cutter.

19. An apparatus comprising:
   (a) a body;
   (b) a cannula extending distally from the body, the cannula including:
      (i) a distal end, and
      (ii) a lateral aperture located proximal to the distal end;
   (c) a cutter positioned within the cannula and configured to sever tissue protruding through the lateral aperture;
   (d) a cutter rotation member unitarily secured to the cutter and configured to translate and rotate unitarily with the cutter;
   (e) a receiving member associated with the body, the receiving member defining a bore and an engagement feature, the bore being configured to receive the cutter rotation member, the engagement feature being configured to cooperate with the cutter rotation member to drive rotation of the cutter in response to longitudinal motion of the cutter; and
(f) a linear actuator configured to drive the cutter longitudinally, the linear actuator including:
 (i) a pneumatic cylinder coupled with the body, and
 (ii) a piston slidably disposed within the pneumatic cylinder, the piston being coupled with the cutter.

20. A method of operating an apparatus, the apparatus comprising:
(a) a body;
(b) a cannula extending distally from the body, the cannula including:
 (i) a distal end, and
 (ii) a lateral aperture located proximal to the distal end;
(c) a cutter positioned within the cannula, the cutter being configured to sever tissue protruding through the lateral aperture;
(d) a cutter rotation member unitarily secured to the cutter, the cutter rotation member being configured to translate and rotate unitarily with the cutter;
(e) a receiving member associated with the body, the receiving member being configured to cooperate with the cutter rotation member to drive rotation of the cutter in response to longitudinal motion of the cutter; and
(f) a linear actuator, the linear actuator being configured to drive the cutter longitudinally;

the method comprising:
(a) activating the linear actuator to drive the cutter proximally from a distal position toward a proximal position using a rod of the linear actuator with the rod being driven linearly relative to a body of the linear actuator while permitting rotation of the cutter, the cutter rotation member and the receiving member cooperating to rotate the cutter while the cutter is driven proximally by the rod;
(b) receiving tissue through the lateral aperture;
(c) activating the linear actuator to drive the cutter distally from the proximal position toward the distal position using the rod with the rod being driven linearly relative to the body of the linear actuator while permitting rotation of the cutter, the cutter rotation member and the receiving member cooperating to rotate the cutter while the cutter is driven distally by the rod; and (d) severing at least some of the received tissue with the cutter as the cutter travels distally from the proximal position toward the distal position.

\* \* \* \* \*